United States Patent [19]
Pines et al.

[11] Patent Number: 5,852,024
[45] Date of Patent: Dec. 22, 1998

[54] TREATMENT AND PREVENTION OF ADHESIONS

[75] Inventors: Mark Pines, Rehovot; Arnon Nagler, Jerusalem, both of Israel

[73] Assignees: Hadasit, Jerusalem; Agricultural Research Organization, Bet Pagan, both of Israel

[21] Appl. No.: 797,701

[22] Filed: Feb. 11, 1997

[51] Int. Cl.$^6$ ................................................ A61K 31/505
[52] U.S. Cl. ............................................................ 514/259
[58] Field of Search ............................................. 514/259

[56] References Cited

U.S. PATENT DOCUMENTS 5,449,678  9/1995  Pines et al. ............................. 514/259

OTHER PUBLICATIONS

Knighton, et al., "Regulation of Cutaneous Wound Healing by Growth Factors and the Microenvironment", *Investigative Radiology*, vol. 26, No. 6,pp. 604–611, (1991).
Haukipuro et al., "Synthesis of Typr I Collagen in Healing Wounds in Humans", *Ann of Surg.*, vol. 213, No. 1 pp. 75–80, (1991).
Granot et al., "Increased Skin Tearing in Broilers and Reduced Collagen Synthesis in Skin in Vivo and In Vitro In Response to the Coccidiostat Halofuginone", *Poultry Science*, 70:1559–1563 (1991).
Ashcroft, The Effects of Ageing on Cutaneous Wound Healing in Mammals, *J. Anat.*, vol. 187, pp. 1–26, (1995).
Choi et al, "Halofuginine, A Specific Collagen Type I Inhibitor, Reduces Anastomic Intimal Hyperplasia" *Arch. Surg.*, vol. 130, pp. 257–261, (1995).
Freidman, et al. "Regulation in Collagen Gene expression in Keloids and Hypertrophic Scars",*J. Surg. Res.*, 55:214–222 (1993).
Rockwell, et al., "Keloids and Hypertrophic Scars: A Comprehensive Review", *Plastic and Recon. Surg.*, vol. 84, No. 5, pp. 827–836, (1989).
Dauo–Brown, D.D., "Keloids: A Review of the Literature", *Brit. J. Plastic Surg.*, 43:70–77, (1990).
Nagler, et al., "Inhibition of Collagen Synthesis, Smooth Muscle Cell Proliferation, and Injury–Induced Intimal Hyperplasia by Halofuginone", *Arter., Thromb. & Vasc. Biol.*, vol. 17, No. 1, pp. 1–9 (1997).
Tulandi, T., "Prevention of Postoperative Intra–Abdominal Adhesions", *Curr. Opin. In Obst. & Gyn.*, 2:87–290,(1990).
Menzies, D., "Postoperative Adhesions: Their Treatment and relevance in Clinical Practice", Ann. Roy. Col. Surg., vol. 75, 147–153, (1993).
Drollette, et al, "Pathophysiology of Pelvic Adhesions", *J. Reprod. Med.*, vol. 37, No. 2, pp. 107–122 (1992).
Monk et al., "Adhesions after Extensive Gyneclogic Surgery: Clinical Significance, Etiology and Prevention",*Am. J. Obstet.Gynecol*, vol. 170, No. 5, Part 1, pp. 1396–1403 (1994).
Glinski et al, "Alterations of T–cell Extracellular Matrix Proteins interctions in Psiorasis", 1993, 153–157.

Holz et al, "Inhibition of Peritoneal Adhesion Reformation After Lysis with Thirty–Two Percent Dextran 70",*Fertility and Sterility*, vol. 34, No. 4, pp. 394–395 (1980).
Menzies et al, "Intra–Abdominal Adhesions and Thei Prevention by Topical Tissue Plasminogen Activator",*J. Roy. Soc. Med.*, vol. 82 pp. 534–535 (1989).
Raftery, A.T., "Effect of Peritoneal Trauma on Peritoneal Fibrinolytic Activity and Intraperitoneal Adhesion Formation", *Eur. Surg. Res.*, 13:397–401 (1981).
Rivkind et al, "Urokinase Does Not Prevent Abdominal Adhesion Formation in Rats", *Eur. Surg. Res.*, 17:254–258 (1985).
Weibel et al, "Peritoneal Adhesions and their Relation to Abdominal Surgery",*Am. J. Of Surg.*, vol. 126, pp. 345–353 (1973).
Gilmore et al "Prevention of Peritoneal Adhesions by a New Providone–Iodine/PVP Solution", J. Of Surg. Res., *J. Of Surg. Res.*, vol. 25, pp. 477–481 (1978).
Rivkind et al, Cianidanol ([+]–Cianidanol–3) Prevents the Development of Abdominal Adhesions in Rats),*Arch. Surg.*, vol. 118, pp. 1431–1433 (1983).
Menzies et al, "The Role Plasminogen Acrivator in Adhesion Prevention", *Surg. Gynecol. & Obstet.*, vol. 172, pp. 361–366 (1991).
Brooks et al "Integrin $\alpha_v\beta_3$ Antagonists Promote Tumor Regression by Inducing Apoptosis of Angeogenic Blood Vessels", *Cell*, vol. 79, pp. 1157–1164 (1994).
Folkman et al, "Angiogenesis", *J. Of Biological Che*, vol. 267 No. 16, pp. 109031–109109 (1992).
Folkman et al, "Angiogenic Factors", *Science*, vol. 235, pp. 442–447 (1987).
Folkman, J., "Toward an Understanding of Angiogenisis: Search & Discovery", *Persp. In Biol. & Med.*, pp. 11–37 (1985).
Salo et al, "Effect of Phenytoin and Nifedipine on Collagen Gene expression in Human Gingival Fibroblasts", 1990; 19:404–7.
Nickoloff et al, "Abberant Production of Interluekin–8 and Thrombospondin–1 by Psoriatic Keratinocytes Mediates Angiogenesis", *Am. J. Path.* vol. 144, No. 4, pp. 820–828 (1994).
Mahadean et al, "The Effects of Ovarian Adhesive Disease Upon Follicular Development in Cycles of Controlled Stimulation for In Vitro Fertilization", Fertility & Sterility, vol. 44, No. 4, pp. 489–492 (1985).

(List continued on next page.)

*Primary Examiner*—Phyllis G. Spivack
*Attorney, Agent, or Firm*—Mark M. Friedman

[57] ABSTRACT

An inhibitor of adhesion formation which can be used to prevent adhesions within the abdominal cavity, particularly following surgical intervention, trauma or inflammation in the area is disclosed. Specifically, the most preferred compound of the present invention, Halofuginone, can be used to prevent collagen deposition from occurring within the peritoneum after surgical intervention, thereby inhibiting adhesion formation. Halofuginone, and related compounds, are useful in the prevention and treatment of both inflammatory and surgically induced adhesions, and in the treatment of congenital adhesions.

20 Claims, 5 Drawing Sheets

OTHER PUBLICATIONS

Takahashi et al, "Cellular Markers That Distinguish the Phases of Hemangioma during Infancy and Childhood", *J. Clin. Invest.*, vol. 93, ppo. 2357–2364 (1994).

Weidner et al, "Tumor Angiogenisis Correlates with Metastasis in Invasive Prostrate Carcinoma", *Am. J. Path.*, vol. 143, No. 2, pp. 401–409 (1993).

Folkman, J., "What is the Evidence That Tumors are Angiogenesis dependent?", J. Nat'l. Cancer Inst., vol. 82, No. 1, pp. 4–6, (1989).

Peacock et al, "Angiogenesis Inhibition Suppresses Collagen Arthritis", *J. Exp. Med.*, vol. 175, pp. 1135–1138 (1992).

Miller et al "Vascular Endothelial Growth factor/Vascular Permeability factor is tempoarilyand Spatially Correlated with Ocular Angiogenesis in a Primate Model", *Am. J. Path.*, vol. 145, No. 3, pp. 574–584 (1994).

Folkman, J., "Angiogenesis in Cancer, Vascular, Rheumatoid and Other Disease", *Nature Medicine*, vol. 1, No. 1, pp. 27–31 (1995).

Bischoff, J. "Approaches to Studying Cell Adhesion Molecules in Angiogenesis", *Trends in Cell Bio.*, vol. 5, pp. 69–74 (1995).

Sawhney et al "Optimization of Photopolymerized Bioerodable Hydrogel Properties for Adhesion Prevention", *J. Biomed. Mat. Res.*, vol. 28, pp. 831–838 (1994).

Jackson et al, "Type 1 Collagen Fibrils Promote Rapid Vascular Tube Formation Upon Contact with the Apical Side of Cultured Endothelium", *Exp. Cell Res.*, 192:319–323 (1991).

Iruela–Arispe et al, "Differential Expression of Extracellular Proteins is Correlated with Angiogenesis In Vitro", *Lab. Invest.*, vol. 64, No. 2, pp. 174–186 (1991).

Ingber et al, "Synthetic Analogues of Fumagillin that Inhibit Angiogenesis and Suppress Tumor Growth", *Nature*, vol. 348, pp. 555–557 (1990).

Castle et al, "Antisense–Mediated Reduction in Thrombospondin Reverses the Mlignant Phenotype of a Human Squamous Carcinoma", *J. Cli. Invest.*, vol. 87, pp. 1883–1888 (1991).

Hill–West et al, "Efficacy of a Resorable Hydrogel Barrier, Oxidized Regenerated Cellulose, and Hyaluronic Acid in the Prevention of Ovarian Adhesions in a Rabbit Model", *Fertility & Sterility*, vol. 62, No. 3, pp. 630–634 (1994).

Vick., "Statistics of Acute Intestinal Obstruction" *Brit. Med. J.*, pp. 546–548 (1932).

Nyska et al., Connect. Tissue Res., 34(2), 97–103 (1996).

Choi et al., Archives of Surgery, 130, 257–261 (Mar., 1995).

TREATMENT AND PREVENTION OF ADHESIONS

FIELD AND BACKGROUND OF THE INVENTION

The present invention relates to a composition and a method for the treatment and prevention of adhesions, and for the promotion of wound healing, and, more particularly, to a composition and a method for the treatment and prevention of pathological processes associated with wound healing, such as the formation of adhesions within the abdominal-pelvic cavity.

Wound healing is a complex process involving such factors as cells, extracellular matrix (ECM) components and the cellular microenvironment. Essentially, all wound healing involves the repair or replacement of damaged tissues. The precise nature of such repair or replacement depends upon the tissues involved, although all such processes involve certain basic principles. To illustrate these principles, cutaneous, or skin, wound healing will be described, it being understood that the discussion could also extend to all types of wound repair.

Skin has three layers, keratin, epidermis and dermis. If only the epidermis is damaged, as in most minor injuries, keratinocytes migrate from the edge of wound and eventually cover it, reforming the epidermis and keratin [D. R. Knighton and V. D. Fiegel, Invest. Radiol., Vol 26, p 604–611, 1991]. The risk of scar formation is thus relatively low for such minor injuries.

If all three skin layers are damaged or destroyed, new connective tissue, called granulation tissue, must first fill the wound space. This tissue is formed by deposition of ECM components by fibroblasts, which migrate into the wound space [D. R. Knighton and V. D. Fiegel, Invest Radiol., Vol 26, p. 604–611, 1991]. Although the formation of granulation tissue is clearly an important protective mechanism, it can also lead to the formation of scars. Production of ECM components, such as collagen, has been particularly linked to scar formation. Scars on the skin can be both a cosmetic and a functional problem. For example, scar formation following serious burns can restrict the nobility of joints. Scar formation within other types of tissue, such as in the lungs after a bacterial infection, or in many organ tissues following surgery, can be extremely dangerous. One reason scars within organ tissues are so dangerous is that the scar does not duplicate the functionality of the original organ tissue, so that the healing of the wound does not lead to a complete restoration of organ capacity and function. Thus, clearly scar formation can be a pathological process.

However, the deposition of ECM components, such as collagen, is currently believed to also be important for healing of the wound. Indeed, the prior art teaches that the strength of the healing wound is ultimately dependent upon collagen deposition [Haukipuro, K., et al., Ann. Surg., Vol 213, p. 75–80, 1991]. Thus, according to the prior art, collagen deposition must be present at a sufficient level to give the healing wound strength and support, yet not at such a high level to cause the formation of scars.

Another pathological process involved in the repair of damaged tissue is the formation of adhesions. The formation of adhesions between organs of the abdominal or pelvic cavities is a frequent and undesirable complication of abdomino-pelvic surgery. Surgical trauma to the tissue causes the release of a serosanguinous exudate, which forms a fibrous bridge that persists over the 4–5 days required for remesothelialization [Hill-West, J. L., et al., Obstet. Gynecol., Vol 83, p. 59–64, 1994; Sawhney, A. S., et al., Macromolecules, Vol 26, p. 581–587, 1993]. If the exudate is not absorbed or lysed within this period, it becomes ingrown with fibroblasts. Subsequent collagen production and deposition from these fibroblasts directly causes the formation of permanent scar tissue, which can connect the traumatized tissue to another organ, for example [Mahadevan et al., Fertil. Steril., Vol 44, p. 489–92, 1985]. Such permanent scar tissue is called an adhesion. Adhesions may be classified as either acquired (90%) or congenital (10%). The acquired type of adhesion is farther classified into inflammatory or post surgical, the majority being post surgical.

Hereinafter, the term "abdominal adhesion" will include adhesions in both the abdominal and pelvic cavities.

For example, patients undergoing multiple abdominal surgeries can have adhesion rates of up to 93% [Weibel, M. A. and G. Manjo, Am. J. Surg., Vol 126, p. 345–353, 1973]. Post-operative adhesions occur in 60–90% of patients undergoing major gynecological surgery [Monk, B. J. et al., Am. J. Obstet. Gynecol., Vol. 170, p. 1396–1403, 1994]. Thus, adhesions occur at an extremely high rate in patients who have undergone surgery in the abdominal area.

Adhesions can cause a number of further complications, such as intestinal obstruction. About 30–60% of patients who develop intestinal obstructions due to adhesions will require surgery, and a further 11–21% will develop recurrent obstructions [Menzies, D., Ann. Royal Col. Surg. Engl., Vol 75, p. 147–153, 1993]. Thus, these complications are serious and require substantial further treatment, thereby increasing both the trauma to the patient and the cost of the surgery. Indeed, in one surgical unit, 1% of all surgical admissions and 3% of all laparotomies were required for treatment of adhesions [Menzies, D., Ann. Royal Col. Surg. Engl., Vol 75, p. 147–153, 1993]. Furthermore, the frequency of intestinal obstructions caused by adhesions has increased steadily, from 7% in 1932 to about 60% in 1993 [Vick, R. M., Br. Med. J., Vol 2, p. 546–548, 1932; Menzies, D., Ann. Royal Col. Surg. Engl., Vol 75, p. 147–153, 1993]. Thus, clearly the problem of adhesion-related complications is growing and methods for treating and preventing adhesions are clearly needed.

Other adhesion-related complications which can arise after pelvic surgery include chronic pelvic pain, voiding dysfunction and infertility [Monk, J. B. et al., Am. J. Obstet. Gynecol., Vol. 170, p. 1396–1403, 1994]. Adhesions can also arise from pelvic inflammatory disease, which is an important cause of infertility [Monk, J. B. et al., Am. J. Obstet. Gynecol., Vol. 170, p. 1396–1403, 1994]. Drugs such as cyclosporine can also cause adhesions and retroperitoneal fibrosis [D. M. Davies, ed., Textbook of Adverse Drug Reactions, Third Edition, Oxford University Press]. Thus, adhesions have many causes and can have serious and far-ranging consequences.

Unfortunately, no currently available method of treating and preventing adhesions is successful, particularly for blocking the mechanism of adhesion formation. For example, povidone-iodine was found to reduce the number of peritoneal adhesions after surgery by 35% in rats, but this effect was due to an anti-microbial effect, rather than a direct inhibition of adhesion formation [Gilmore, O. J. A. and C. Reid, J. Surg. Res., p. 477–481, 1978]. Another drug, dextran, was used by gynecological surgeons for adhesive prevention in infertility surgery but with little success [Holtz, G. et al., Fertil. Steril., Vol 33, p. 660, 1980]. Other compounds which have been tried include various plasminogen activators and fibrinolytic agents. These compounds were used because of the known fibrinolytic property of the peritoneum, resulting from the production of plasminogen activator. This production is reduced following trauma to the peritoneum, which may allow fibrin to form adhesions between traumatized areas [Raferty, A. T., Eur. Surg. Res., Vol 13, p. 397–401, 1981]. However, attempts to block fibrin deposition by using plasminogen activators and/or fibrinolytic agents has not proved routinely successful in rats, although some success was reported in rabbits [Rivkind, A. I., et al., Eur. Surg. Res., Vol 17, p. 254–258, 1985; Menzies, D. and H. Ellis, J. R. Soc. Med., Vol 82, p. 534–553, 1989]. Thus, currently available pharmacological methods are clearly not completely successful for the treatment or prevention of adhesions.

Non-pharmacological methods which have been tried include the use of polymeric or biological mechanical barriers to isolate a traumatized region from surrounding organs and other peritoneal tissues. However, these barriers have only had limited success in animal models [Sawhney, A. S., et al., J. Biomed. Mater. Res., Vol 28, p. 831–838, 1994; Sawhney, A. S., et al., Macromolecules, Vol 26, p. 581–587, 1993]. Furthermore, barrier methods have the disadvantage of requiring direct internal application to the site of trauma, rather than allowing systemic application.

As noted above, collagen deposition is an important step in the mechanism of adhesion formation, as well as in scar formation. If collagen deposition were prevented, adhesions and permanent scars might not be formed. Thus, these pathological processes are caused, at least in part, by the synthesis of excess collagen. Furthermore, the crucial role of collagen in other clinical conditions, such as fibrosis, has prompted attempts to develop drugs that inhibit its accumulation [K. I. Kivirikko, *Annals of Medicine*, Vol. 25, pp. 113–126 (1993)].

Such drugs can act by modulating the synthesis of the procollagen polypeptide chains, or by inhibiting specific post-translational events, which will lead either to reduced formation of extra-cellular collagen fibers or to an accumulation of fibers with altered properties. Unfortunately, only a few inhibitors of collagen synthesis are available, despite the importance of this protein in sustaining tissue integrity and its involvement in various disorders.

For example, cytotoxic drugs have been used in an attempt to slow the proliferation of collagen-producing fibroblasts [J. A. Casas, et al., *Ann. Rhem. Dis.*, Vol. 46, p. 763 (1987)], such as colchicine, which slows collagen secretion into the extracellular matrix [D. Kershenobich, et al., *N. Engl. J. Med.*, Vol. 318, p. 1709 (1988)], as well as inhibitors of key collagen metabolism enzymes [K. Karvonen, et al., *J. Biol Chem.*, Vol. 265, p. 8414 (1990); C. J. Cunliffe, et al., *J. Med. Chem.*, Vol. 35, p.2652 (1992)].

Unfortunately, none of these inhibitors are collagen-type specific. Also, there are serious concerns about the toxic consequences of interfering with biosynthesis of other vital collagenous molecules, such as Clq in the classical complement pathway, acetylcholine esterase of the neuro-muscular junction endplate, conglutinin and pulmonary surfactant apoprotein.

Certain other drugs which can inhibit collagen synthesis, such as nifedipine and phenytoin, inhibit synthesis of other proteins as well, thereby non-specifically blocking the collagen biosynthetic pathway [T. Salo, et at. *J. Oral Pathol. Med.*, Vol. 19, p. 404 (1990)]. Even a drug which was relatively more specific for collagen synthesis, cianidanol, proved to be toxic because of its effects on the synthesis of many types of collagen and because of its effect on other Fe++ ion-binding enzymes, in spite of its ability to decrease the number of post-surgical adhesions in rats [Rivkind, A. I., et al., Arch. Surg., Vol 118, p. 1431–1433, 1983]. Thus, simply preventing adhesion formation alone does not make a compound useful if it is sufficiently non-specific to cause toxic side effects.

Collagen cross-linking ihibitors, such as β-aminopropionitrile, are also non-specific, although they can serve as useful anti-fibrotic agents. Their prolonged use causes lathritic syndrome and interferes with elastogenesis, since elastin, another fibrous connective tissue protein, is also cross-linking. In addition, the collagen cross-linking inhibitory effect is secondary, and collagen overproduction has to precede its degradation by collagenase. Thus, a type-specific inhibitor of the synthesis of collagen itself is clearly required as an anti-fibrotic agent.

Such a type-specific collagen synthesis inhibitor was found by observing chickens which were fed extremely high levels of the coccidostat Halofuginone. These chickens were found to have fragile, weakened skin, as evidenced by increased skin tearing, which was caused by the inhibition of collagen synthesis [Granot, I. et al., *Poultry Sci.*, Vol 70, p. 1559–1563, 1991]. Halofuginone and related compounds are disclosed in U.S. Pat. No. 5,449,678 for the treatment of a fibrotic condition, as a composition with a pharmaceutically effective amount of a pharmaceutically active compound of a formula:

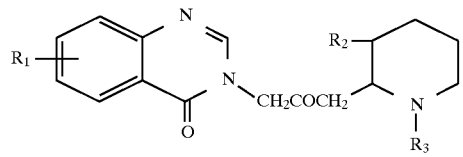

wherein:

$R_1$ is a member of the group consisting of hydrogen, halogen, nitro, benzo, lower alkyl, phenyl and lower alkoxy;

$R_2$ is a member of the group consisting of hydroxy, acetoxy and lower alkoxy, and $R_3$ is a member of the group consisting of hydrogen and lower alkenoxy-carbonyl.

Of this group of compounds, Halofuginone has been found to be particularly effective for such treatment.

U.S. Pat. No. 5,449,678 discloses that these compounds are effective in the treatment of fibrotic conditions such as scleroderma and GVHD. WO No. 96/06616 further discloses that these compounds are effective for the treatment of restenosis, as they prevent vascular smooth muscle cell proliferation. Furthermore, Halofuginone has been shown to be effective in the prevention of adhesions between a surgically traumatized tendon and its sheath in chickens [Nyska, M. et al., *Conn. Tissue Res.*, Vol 34, p. 97–103, 1996]. However, none of these studied models adequately predicts the behavior of Halofuginone in the promotion of wound healing or the prevention of abdominal adhesions for a number of reasons.

First, the prior art teaches against the use of Halofuginone to promote wound healing, since as described above, the prior art teaches that collagen is necessary for wound healing. According to the prior art, collagen is particularly necessary for the strength of the wound. Thus, any use of Halofuginone to reduce or prevent scar formation might be expected to also prevent the healing of the wound.

Second, the prior art does not teach the efficacy of Halofuginone in the treatment or inhibition of adhesions, since tendons and abdominal tissues have very different structures and compositions. Tendons are mainly collagen. When a tendon is damaged, new collagen synthesis must take place for the tendon to be repaired. It is easy to see how excess collages deposition could lead to the formation of adhesions between the tendon and its sheath, since such excess deposition could simply be the result of a slight oversynthesis of collagen during the repair of the tendon. Thus, inhibition of collagen synthesis should be expected to prevent the attachment of the tendon to its sheath.

By contrast, abdominal tissue has multiple layers. These layers include many different types of cells. However, none of these cells normally synthesize collagen. Instead, the mechanism of adhesion formation requires a complex interaction between fibrin, fibroblasts and the tissue of the peritoneum. It is not obvious that simply inhibiting one portion of this interaction would be successful in preventing the formation of adhesions, since this was tried with plasminogen activators and fibrolytic agents, as described above. These compounds also inhibit one portion of the mechanism of adhesion formation, yet they were not fully successful in preventing such formation. Such lack of success is particularly surprising since these compounds inhibit a relatively early stage in the process, where the chance of success might be considered comparatively greater. Thus, the mere inhibition of one step of adhesion formation does not appear to be sufficient to prevent such formation, or the related complications such as intestinal obstruction.

Next, the involvement of collagen type I in the formation of abdominal adhesions has not been previously demonstrated in the prior art. However, Halofuginone only inhibits the synthesis of collagen type I, and does not inhibit the synthesis of other collagens, such as α2(I), type II, type III or type X [Granot, I. et al., Biochim. Biophys. Acta., Vol 1156, p. 107–112, 1993; Choi, E. T. et al., Arch. Surg., Vol 130, p. 257–261, 1995]. Thus, the ability of Halofuginone to prevent the formation of abdominal adhesions cannot be predicted from the prior art, since such adhesions could have arisen from any one of these different types of collagen.

Finally, the route of administration in the study of Nyska et al. in chickens [Nyska, M. et al., *Conn. Tissue Res.*, Vol 34, p. 97–103, 1996] involves tendons that were locally treated with Halofuginone through a catheter. Similarly, the barrier methods described above also require the direct administration of the barrier compound at the adhesion site. However, such a route makes treatment with Halofuginone impractical, since the treatment can then only occur during a surgical intervention. For certain types of adhesions, such as those caused by pelvic inflammatory disease, surgical intervention is not necessarily desirable. By contrast, much more efficient routes of administration would include systemic treatment, for example oral or parenteral administration. Such routes would permit treatment without any prior surgical intervention, as well as both pre- and post-operative treatment with Halofuginone, which could be particularly critical if complications develop substantially after surgery. Furthermore, systemic treatment should reduce or eliminate the need for further surgical intervention, which is not necessarily true for barrier or barrier-like methods of treatment.

There is thus a widely recognized need for, and it would be highly advantageous to have, a promoter of wound healing which substantially inhibits such pathological processes as adhesion formation, which can be administered pre- or post-operatively, or both, or substantially without prior surgical intervention, and which substantially prevents or reduces the formation of scars in the skin and other organs, as well as the formation of adhesions within the abdomen, particularly following surgical insult to tissue in the abdominal cavity, without causing non-specific effects.

SUMMARY OF THE INVENTION

According to the present invention, there is provided a composition and a method for treating an adhesion, the composition including a pharmaceutically effective amount of a compound in combination with a pharmaceutically acceptable carrier, the compound being a member of a group having a formula:

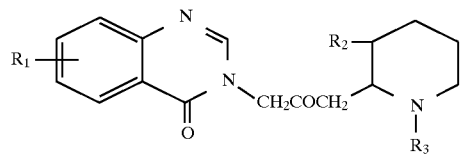

wherein:

$R_1$ is a member of the group consisting of hydrogen, halogen, nitro, benzo, lower alkyl, phenyl, and lower alkoxy;

$R_2$ is a member of the group consisting of hydroxy, acetoxy, and lower alkoxy, and $R_3$ is a member of the group consisting of hydrogen and lower alkenoxy.

According to another embodiment of the present invention, there is provided a method of manufacturing a medicament for treating an adhesion, including the step of placing a pharmaceutically effective amount of a compound in a pharmaceutically acceptable carrier, the compound being a member of a group having a formula:

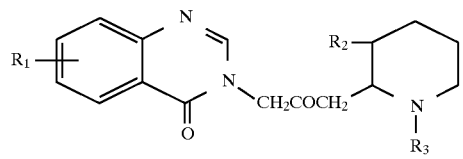

wherein:

$R_1$ is a member of the group consisting of hydrogen, halogen, nitro, benzo, lower alkyl, phenyl, and lower alkoxy;

$R_2$ is a member of the group consisting of hydroxy, acetoxy, and lower alkoxy, and $R_3$ is a member of the group consisting of hydrogen and lower alkenoxy-carbonyl.

According to still another embodiment of the present invention, there is provided a method of manufacturing a medicament for substantially inhibiting formation of an adhesion, including the step of placing a pharmaceutically effective amount of a compound in a pharmaceutically acceptable carrier, the compound being a member of a group having a formula:

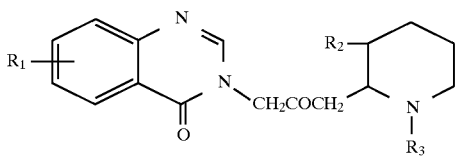

wherein:

$R_1$ is a member of the group consisting of hydrogen, halogen, nitro, benzo, lower alkyl, phenyl, and lower alkoxy;
$R_2$ is a member of the group consisting of hydroxy, acetoxy, and lower alkoxy, and
$R_3$ is a member of the group consisting of hydrogen and lower alkenoxy-carbonyl.

According to still another embodiment of the present invention, there is provided a method and a composition for substantially preventing formation of an adhesion, including the step of administering a pharmaceutically effective amount of a compound having a formula:

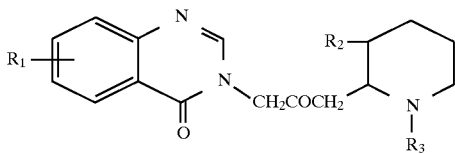

wherein:

$R_1$ is a member of the group consisting of hydrogen, halogen, nitro, benzo, lower alkyl, phenyl, and lower alkoxy;
$R_2$ is a member of the group consisting of hydroxy, acetoxy and lower alkoxy, and
$R_3$ is a member of the group consisting of hydrogen and lower alkenoxy-carbonyl.

According to other embodiments of the present invention, there is provided a method of manufacturing a medicament for treatment substantially before a performance of a surgical procedure for inhibition of formation of an adhesion, including the step of placing a pharmaceutically effective amount of a compound in a pharmaceutically acceptable carrier, the compound being a member of a group having a formula:

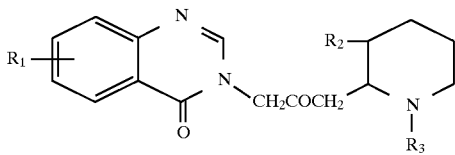

wherein:

$R_1$ is a member of the group consisting of hydrogen, halogen, nitro, benzo, lower alkyl, phenyl, and lower alkoxy;
$R_2$ is a member of the group consisting of hydroxy, acetoxy, and lower alkoxy, and
$R_3$ is a member of the group consisting of hydrogen and lower alkenoxy-carbonyl.

According to still other embodiments of the present invention, there is provided a composition for treatment substantially before a performance of a surgical procedure for inhibition of formation of an adhesion, including a pharmaceutically effective amount of a compound having a formula:

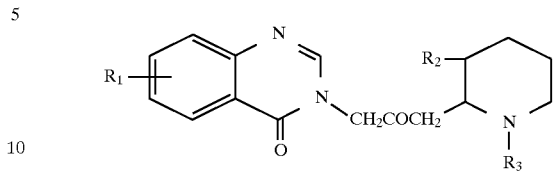

wherein:

$R_1$ is a member of the group consisting of hydrogen, halogen, nitro, benzo, lower alkyl, phenyl, and lower alkoxy;
$R_2$ is a member of the group consisting of hydroxy, acetoxy and lower alkoxy, and
$R_3$ is a member of the group consisting of hydrogen and lower alkenoxy-carbonyl.

A method of use of this composition is also provided.

According to still other embodiments of the present invention, there is provided a method of manufacturing a medicament for treatment of an inflammatory disease characterized by formation of an adhesion, including the step of placing a pharmaceutically effective amount of a compound in a pharmaceutically acceptable carrier, the compound being a member of a group having a formula:

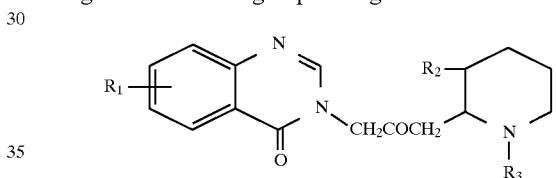

wherein $R_1$ is a member of the group consisting of hydrogen, halogen, nitro, benzo, lower alkyl, phenyl, and lower alkoxy;
$R_2$ is a member of the group consisting of hydroxy, acetoxy, and lower alkoxy, and
$R_3$ is a member of the group consisting of hydrogen and lower alkenoxy-carbonyl.

According to yet another embodiment of the present invention, there is provided a composition for treatment of an inflammatory disease characterized by formation of an adhesion, including a pharmaceutically effective amount of a compound having a formula:

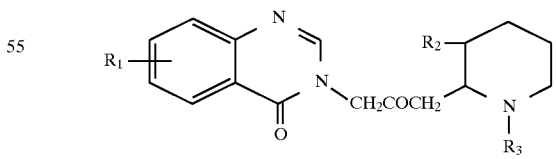

wherein:

$R_1$ is a member of the group consisting of hydrogen, halogen, nitro, benzo, lower alkyl, phenyl, and lower alkoxy;
$R_2$ is a member of the group consisting of hydroxy, acetoxy and lower alkoxy, and $R_3$ is a member of the group consisting of hydrogen and lower alkenoxy-carbonyl.

There is also provided a method of use of the composition. Preferably, the inflammatory disease in each of the above embodiments is pelvic inflammatory disease.

According to yet another embodiment of the present invention, there is provided a method of manufacturing a medicament for treatment of an inflammatory disease characterized by formation of an adhesion, including the step of placing a pharmaceutically effective amount of an antibiotic with a pharmaceutically effective amount of a second compound in a pharmaceutically acceptable carrier, the second compound being a member of a group having a formula:

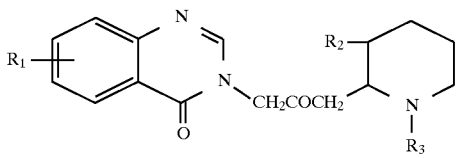

wherein:

$R_1$ is a member of the group consisting of hydrogen, halogen, nitro, benzo, lower alkyl, phenyl, and lower alkoxy;

$R_2$ is a member of the group consisting of hydroxy, acetoxy, and lower alkoxy, and $R_3$ is a member of the group consisting of hydrogen and lower alkenoxy-carbonyl.

There is also provided a composition for treatment of an inflammatory disease characterized by formation of an adhesion, including a pharmaceutically effective amount of an antibiotic and a pharmaceutically effective amount of a second compound having a formula:

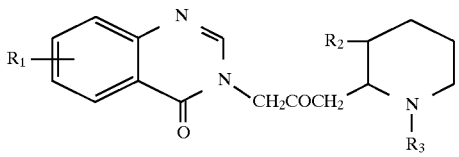

wherein:

$R_1$ is a member of the group consisting of hydrogen, halogen, nitro, benzo, lower alkyl, phenyl, and lower alkoxy;

$R_2$ is a member of the group consisting of hydroxy, acetoxy and lower alkoxy, and $R_3$ is a member of the group consisting of hydrogen and lower alkenoxy-carbonyl.

There is also provided a method of use of the composition. Again, preferably in each of the above embodiments, the inflammatory disease is pelvic inflammatory disease.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
FIGS. 1A and 1B illustrate the presence of type I collagen synthesis in adhesions.
Figure 1:

Unexpectedly, the present invention has been found to act as an inhibitor of pathological processes arising from wound healing, such as adhesion and scar formation. The present invention is an inhibitor of adhesion formation which can be used to prevent adhesions within the abdominal cavity including, but not limited to, adhesions following surgical intervention in the area, those caused by foreign bodies such as insulin pumps, adhesions arising from inflammation, trauma, irradiation and tumors, and those caused by drugs such as cyclosporine. The present invention is also an inhibitor of scar formation in organs such as the skin, heart, lungs, liver and kidneys.

Specifically, the most preferred compound of the present invention, Halofuginone, can be used to inhibit scar and adhesion formation, and promote wound healing, by preventing collagen deposition from occurring within the wound space. In examples detailed below, Halofuginone is shown to inhibit collagen deposition within the peritoneum following surgical intervention, thereby inhibiting adhesion formation. As noted above, such inhibition is novel and non-obvious because other compounds which inhibit fibrin deposition have not been shown to be effective, which is particularly surprising since fibrin deposition occurs at a much earlier stage in the process of adhesion formation. Yet, as shown below in studies on an in vivo rat model, Halofuginone succeeds where these other treatments have failed.

In other examples give below, Halofuginone is shown not to interfere with wound healing. Such an effect is particularly unexpected because Halofuginone decreases collagen deposition. However, collagen deposition is required to strengthen the healing wound. Furthermore, high levels of Halofuginone lead to decreased skin strength and increased skin tearing. Based upon the prior art, Halofuginone would be expected to obstruct wound healing. Yet, contrary to the teachings of the prior art, Halofuginone has been specifically shown to promote wound healing, an effect which is both novel and non-obvious.

Based upon these novel, non-obvious and completely unexpected results, Halofuginone could clearly be used in a number of ways for the promotion of wound healing. For example, Halofuginone could be used to either treat formed adhesions, such as those following surgery or inflammatory disease, or to substantially inhibit the formation of those adhesions. Halofuginone could be used to inhibit the formation of scars, such as those arising from surgical interventions or trauma to organs such as the skin, heart, liver and lungs.

Halofuginone can also be used as a pretreatment, administered to a subject before surgery to substantially prevent the formation of scars or adhesions. Of course, such a pretreatment would be most effective for scheduled surgery, as that would allow Halofuginone to be administered for a sufficient period of time before surgery to be most effective.

Another method of treatment would include the administration of Halofuginone, either alone or alternatively and preferably in combination with an antibiotic, for the treatment of inflammatory disease. Such a treatment would be particularly useful for the treatment of pelvic inflammatory disease, in which adhesion formation is induced by a bacterial infection in the reproductive organs of a woman.

The present invention may be more readily understood with reference to the following illustrative examples and figures. It should be noted that although reference is made exclusively to Halofuginone, it is believed that the other quinazolinone derivatives described and claimed in U.S. Pat. No. 3,320,124, the teachings of which are incorporated herein by reference, have similar properties.

EXAMPLE 1

Involvement of Collagen in Adhesion Formation

The involvement of collagen in post-surgical adhesion formation in the abdomens of rats was studied. Briefly, collagen-specific staining techniques, as well as hybridization with a labelled collagen-specific genetic probe, demonstrate the importance of collagen as a component of adhesions, as shown in FIGS. 1A and 1B.

The experiments were performed as follows. First, the abdomen of the rats was shaved and prepared with iodine and alcohol. The abdominal cavity was entered through a mid-line incision. The small intestine was scraped from the duodenum down to from about 9 to about 10 cm from the cecum, until capillary bleeding occurred. To avoid drying, Hartman's solution at about 37° C. was occasionally dripped on the intestine. After replacement of the intestine into the abdominal cavity, the abdomen was closed in two layers with continuous 00 chromic catgut suture. This method has been previously demonstrated to cause abdominal adhesions [Rivkind, A. I. et al., Eur. Surg. Res., Vol 17, p. 254–258, 1985]. After 21 days, the rats were sacrificed and the sutures were reopened to determine the level of adhesion formation and to take biopsies of the tissue.

The tissue was sectioned so that histological studies could be performed. Briefly, the tissue samples were collected into phosphate-buffered saline (PBS) and fixed overnight in 4% paraformaldehyde in PBS at 4° C. Serial 5 μm sections were prepared after the samples had been dehydrated in graded ethanol solutions, cleared in chloroform and embedded in Paraplast. Differential staining of collagenous and non-collagenous proteins was performed with 0.1% Sirius red and 0.1% fast green as a counter-stain in picric acid. This procedure stains collagen red [Gascon-Barre, M., et al., J. Histochem. Cytochem., Vol 37, p. 377–381, 1989].

For hybridization with the genetic probe, the sections were deparafinized in xylene, rehydrated through a graded series of ethanol solutions, rinsed in distilled water for 5 minutes and then incubated in 2× SSC [What is the recipe?] at 70° C. for 30 minutes. The sections were then rinsed in distilled water and treated with pronase, 0.125 mg/ml in 50 mM Tris-HCl, 5 mM EDTA, pH 7.5, for 10 minutes. After digestion, the slides were rinsed with distilled water, post-fixed in 10% formalin in PBS and blocked in 0.2% glycine. After blocking, the slides were rinsed in distilled water, rapidly dehydrated through graded ethanol solutions and air-dried for several hours. Before hybridization, the 1600 bp rat collagen α1(I) insert was cut out from the original plasmid, pUC18, and inserted into the pSafyre plasmid. The sections were then hybridized with this probe after digoxigenin-labelling. Alkaline phosphatase activity was detected in the sections as previously described [Knopov, V., et al., Bone, Vol 16 p. 329S–334S, 1995].

FIG. 1A shows a section of tissue taken from one of the adhesions and stained with Sirius red. An adhesion between two intestinal walls is indicated by the dotted outline and by the arrow. The adhesion is specifically stained by Sirius red, indicating the presence of collagen. FIG. 1B shows that the cells in this adhesion are specifically expressing the collagen α1(I) gene, indicating the presence of collagen type I. Note that each brown dot represents a cell expressing the collagen α1(I) gene. Thus, clearly collagen type I is present in abdominal adhesions induced in the rats.

EXAMPLE 2

Effect of Halofuginone on Collagen Gene Expression and Content

Figure 2:
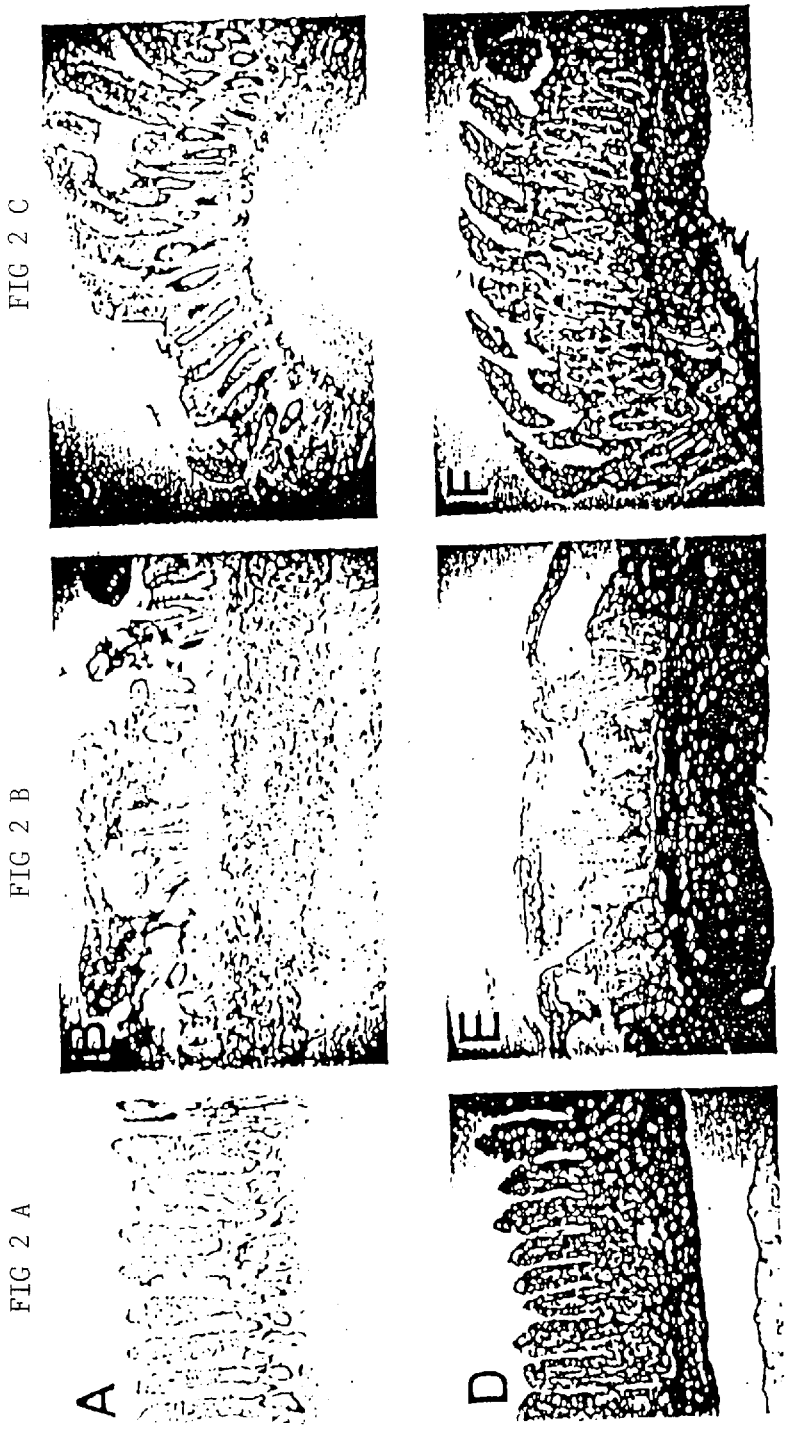
FIGS. 2A–2F illustrate the inhibition of collagen type I synthesis by Halofuginone.

Halofuginone was shown to specifically inhibit collagen type I deposition and gene expression in surgically insulted abdominal tissue in rats, with the results given in FIG. 2. The experiment was performed as follows. Abdominal adhesions were induced in two groups of rats as described above in Example 1. A group of rats which did not undergo surgery served as a control. One group of the rats which underwent surgery received an i.p. injection of Halofuginone every day after the operation for 21 days. The rats were dosed according to body weight, with 1 ug of Halofuginone given per 25 g of body weight. The other group of rats which underwent surgery received saline injections for 21 days.

After 21 days, tissue samples were taken for histological analysis as described above. Both collagen type I content of the tissue, and the level of collagen a(1)I gene expression were measured. The results are shown in FIG. 2.

FIG. 2A shows that almost no collagen α1(I) gene expression was observed in tissue samples from control rats which did not undergo surgery. Corresponding levels of collagen type I content were also low, as shown in FIG. 2D, and the villi are well-organized without any damage.

Tissue samples from rats which underwent surgery, but which were given only saline injections, have both high levels of collagen α1(I) gene expression, as shown in FIG. 2B, and correspondingly high levels of collagen type I, as shown in FIG. 2E. The villi of these animals was heavily damaged, probably due to ischemia.

By contrast, Halofuginone inhibited these pathological processes in surgically treated rats. Tissue samples from rats treated with Halofuginone after surgery show both low levels of collagen α1(I) gene expression, as shown in FIG. 2C, and low level of collagen type I, as shown in FIG. 2F. Indeed, both the level of gene expression and the level of collagen itself were indistinguishable from control rats which did not undergo surgery. Furthermore, much less damage to the villi was observed. Thus, clearly Halofuginone prevented the pathological overstimulation of collagen gene expression and of collagen synthesis in rats which underwent surgical intervention.

EXAMPLE 3

Effect of Halofuginone on Adhesion Number

Two different tests were performed to assess the effect of Halofuginone on the number and severity of adhesions in rats which underwent surgery. Both tests showed that Halofuginone reduced both the number and severity of adhesions. The experimental method was as follows. For the first test, three groups of rats were prepared as described above in Example 2. At the end of 21 days, the rats were weighed and the number and severity of adhesions were determined according to a double-blind procedure.

In the double-blind procedure, adhesions were classified according to the following grading: 0=no adhesions; 1=a thin, filmy, easily separated adhesion; II=several thin adhesions; III=a thick, broad adhesion and IV=several thick adhesions. Clearly, 0 is the least severe and IV is the most severe grade.

Table 1 shows the results of Halofuginone treatment on the number and severity of rats which underwent surgery. Group 1 is rats which underwent surgery, without Halofuginone treatment. Group 2 is rats which underwent surgery with Halofuginone treatment. Group 3 is rats which did not undergo surgery. Clearly, no adhesions were found in control rats which did not undergo surgery. Both the number and severity of adhesions were sharply reduced in Halofuginone-treated rats as compared to non-treated rats, almost to the level seen in rats which did not undergo surgery. A small reduction in weight gain was observed in all rats which underwent surgery, although this reduction was more pronounced in Halofuginone-treated rats.

TABLE 1

Effect of Halofuginone Injection on Adhesion Number and Severity

| Group Number | Weight Gain (g/21 days) | Adhesion Score |
|---|---|---|
| 1 | 24 | 2–3 |
| 1 | 20 | 1–2 |
| 1 | 38 | 2–3 |
| 1 | 36 | 3–4 |
| 1 | 27 | 2–3 |
| 2 | 0 | 0 |
| 2 | 4 | 0–1 |
| 2 | 0 | 2 |
| 2 | 39 | 0 |
| 2 | 13 | 0 |
| 3 | 60 | 0 |
| 3 | 50 | 0 |
| 3 | 70 | 0 |
| 3 | 45 | 0 |
| 3 | 30 | 0 |

In the second experiment, Halofuginone was administered in the diet of two groups of rats at a concentration of 5 mg/kg dry feed for 4 days before surgery, as a pretreatment. Two other groups of rats were fed a normal diet and served as control groups. One of the groups of rats fed Halofuginone and one control group the underwent surgery as described above. Halofuginone treatment was continued for 21 days following surgery, after which the rats were sacrificed and the number and severity of adhesions were determined, and body weight was measured.

Table 2 shows the effect of Halofuginone on adhesion formation. Group 1 is rats which underwent surgery but were not treated with Halofuginone. Group 2 is rats which underwent surgery and were treated with Halofuginone. Group 3 is rats which did not undergo surgery and were treated with Halofuginone. Group 4 is rats which did not undergo surgery and were not treated with Halofuginone. None of the rats without surgical intervention, either with or without Halofuginone treatment, had any adhesions. However, almost all of the rats which underwent surgical intervention, but which were not treated with Halofuginone, had at least one adhesion. Most of the adhesions were between loops of the small bowels and at least one was between the small bowel and the omentum. By contrast, a smaller number of Halofuginone-treated rats which underwent surgery had an adhesion. Thus, clearly Halofuginone administered in the diet, similar to the administration to chickens as a coccidostat, was able to inhibit post-surgical adhesion formation in rats. Furthermore, weight gain by all of the different groups of rats was substantially similar, showing that the effect of Halofuginone was specific and did not result in any general reduction in overall well-being of the rats.

TABLE 2

Effect of Halofuginone in Diet on Adhesion Number and Severity

| Group Number | Weight Gain (g/21 days) | Adhesion Score |
|---|---|---|
| 1 | 70 | 1–2 |
| 1 | 73 | 1 |
| 1 | 80 | 0 |
| 1 | 87 | 1–2 |
| 1 | 93 | 3–4 |
| 1 | 83 | 3 |
| 1 | 92 | 1–2 |
| 1 | 109 | 1–2 |
| 1 | 113 | 3 |
| 1 | 77 | 1–2 |
| 2 | 86 | 0–1 |
| 2 | 76 | 0 |
| 2 | 61 | 1 |
| 2 | 80 | 1–2 |
| 2 | 80 | 0 |
| 2 | 65 | 0 |
| 2 | 90 | 1 |
| 2 | 80 | 0–1 |
| 2 | 79 | 0–1 |
| 2 | 63 | 1–2 |
| 3 | 102 | 0 |
| 3 | 70 | 0 |
| 3 | 73 | 0 |
| 3 | 98 | 0 |
| 3 | 72 | 0 |
| 3 | 90 | 0 |
| 3 | 80 | 0 |
| 3 | 76 | 0 |
| 3 | 85 | 0 |
| 3 | 83 | 0 |
| 4 | 93 | 0 |
| 4 | 80 | 0 |
| 4 | 85 | 0 |
| 4 | 115 | 0 |
| 4 | 100 | 0 |
| 4 | 60 | 0 |
| 4 | 100 | 0 |
| 4 | 102 | 0 |
| 4 | 105 | 0 |
| 4 | 68 | 0 |

EXAMPLE 4

Effect of Halofuginone on Alkaline Phosphatase Activity

High levels of alkaline phosphatase activity were seen in tissue samples from control rats which did not undergo surgery. Alkaline phosphatase activity was substantially completely abolished in tissue from rats which did not undergo surgery, and Halofuginone did not alter this effect. The experiment was performed as follows.

Three groups of rats were prepared as described in Example 2 above, one control group which did not receive Halofuginone and which did not undergo surgery; one group which underwent surgery but did not receive Halofuginone; and one which both underwent surgery and received Halofuginone. After 21 days, tissue samples were taken from all three groups of rats and histological sections were prepared as described in Example 1, and alkaline phosphatase activity was measured as described in Example 1.

Figure 3:
FIGS. 3A–3C illustrate the effect of Halofuginone on alkaline phosphatase activity.

FIG. 3A shows that control rats, which neither underwent surgery nor received Halofuginone, had high levels of alkaline phosphatase activity, particularly at the ends of villi populated by more mature and differentiated cells. By contrast, FIGS. 3B and 3C show that substantially no alkaline phosphatase activity was observed in the rats which underwent surgery, whether injected with saline (FIG. 3B) or Halofuginone (FIG. 3C).

A reduction in alkaline phosphatase activity is typically seen in tissues which have been traumatized, such as during surgical interventions. An increase in TGFβ synthesis following surgically-induced trauma has been implicated in both the reduction in alkaline phosphatase activity and the increase in collagen synthesis observed in traumatized abdominal tissue. Thus, the lack of effect of Halofuginone on alkaline phosphatase activity again demonstrates its specificity of inhibition of collagen synthesis alone, and its lack of effect on other post-traumatic events.

EXAMPLE 5

Effect of Halofuginone on Wound Healing

Figure 4:
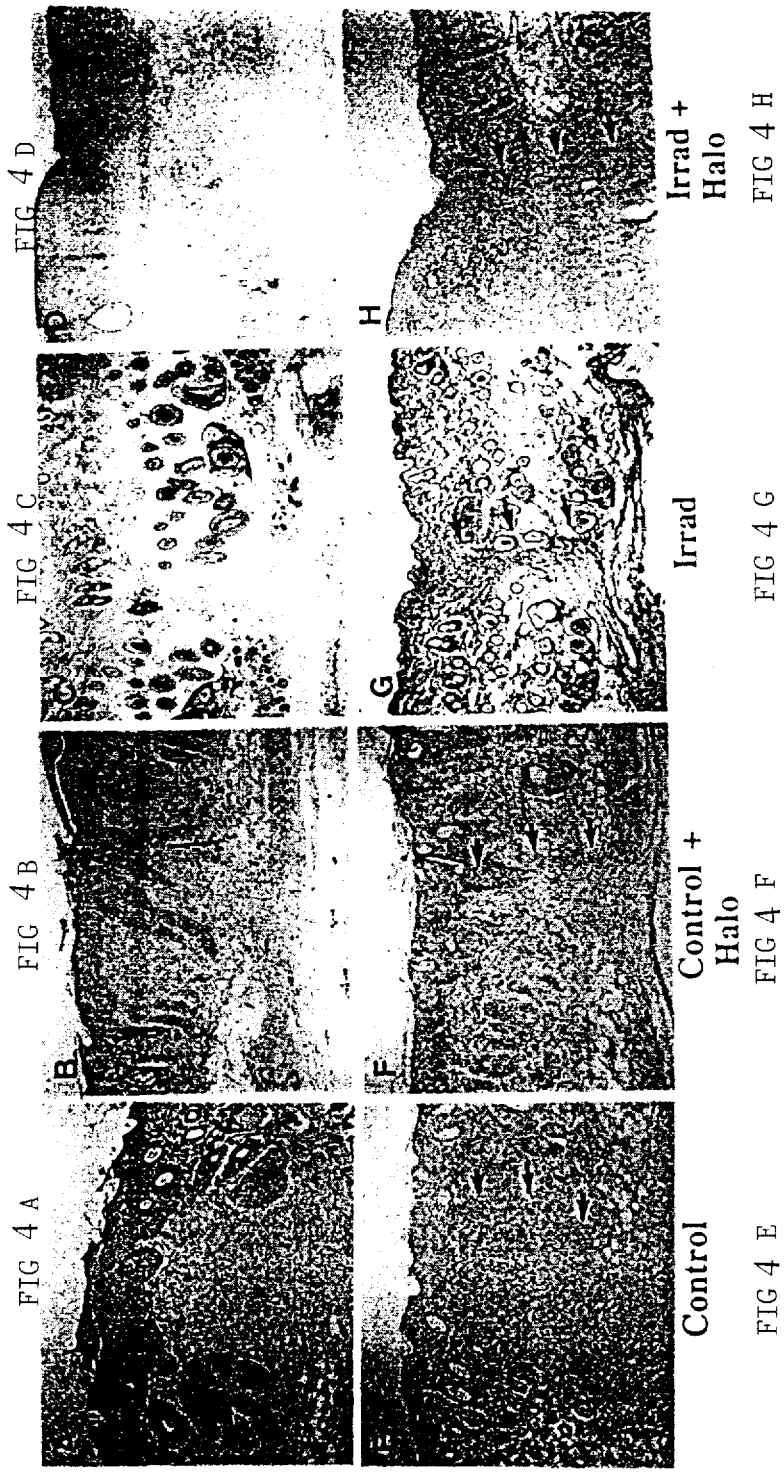
FIGS. 4A–4H illustrate the effect of Halofuginone on wound healing.

The effect of Halofuginone on wound healing was examined by using mice which were first irradiated and then wounded. As shown in FIG. 4, although Halofuginone treatment caused a reduction in the collagen content of the wounded, irradiated skin, the wound still healed.

The experiment was conducted as follows. First, C3H, defined-flora, pathogen-free female mice of 12–14 weeks of age were anesthetized with 60 mg/kg sodium phenobarbital. The mice were then shaved. One group of mice was then irradiated as follows. First, a flap of skin about 40 mm long and about 20 mm wide was pulled through a slit in the lead cover of an irradiation jig and secured with tape, so that only the flap of skin was exposed. This exposed skin was then irradiated by using a 175 kVp/20 mA orthovoltage X-ray source, with a 2 mm Cu filter at a dose rate of 1.0 Gy/min. A standard dose of 18 Gy was delivered.

All of the mice were then wounded by making a full depth incision, about 25 mm long, in the skin along the midline of the lower back. Note that for the irradiated animals, the wound was made within the irradiated area, immediately following irradiation. For all mice, the incision was immediately closed by 3–4 metallic wound closure clips which were removed 2 days later.

After wounding, the mice were injected i.p. every other day, either with 1 μg/mouse Halofuginone or with saline as a control. After 14 days, 2 days following the last injection, the mice were sacrificed and skin samples were collected into phosphate-buffered saline (PBS) and fixed in 4% paraformaldehyde in PBS at 4° C. Serial 5 mm sections were prepared after the samples had been dehydrated in graded ethanol solutions, cleared in chloroform and embedded in Parafin. The sections were deparafinized in xylene, rehydrated through a graded series of ethanol solutions, rinsed in distilled water and treated with 0.125 mg/ml pronase in 50 mM Tris-HCl, 5 mM EDTA, pH 7.5 for 10 minutes. After digestion, slides were rinsed in distilled water, postfixed in 10% formalin in PBS, blocked in 0.2% glycine, rinsed in distilled water again, rapidly dehydrated through a graded ethanol solution and air-dried for several hours. Samples were then stained with hematoxylin-eosin (FIGS. 4A–D). Inmunohistochemistry was performed with specific rabbit immune serum to rat collagen type I (Laboratoire de Pathologie Cellulaire, Institut Pasteur de Lyon, Lyon, France) and secondary rat anti-rabbit FITC-conjugated McAb (FIGS. 4E–H).

FIGS. 4A and 4E show tissue taken from the wound of a mouse treated with saline. FIGS. 4B and 4F show tissue taken from the wound of a mouse treated with Halofuginone. FIGS. 4C and 4G show tissue taken from the wound of an irradiated mouse treated with saline. FIGS. 4D and 4H show tissue taken from the wound of an irradiated mouse treated with Halofuginone. Essentially, FIG. 4G shows that collagen content was higher in the wound of an irradiated mouse. However, FIG. 4H shows that collagen content was significantly lowered by treatment with Halofuginone. Yet, all of these wounds healed, regardless of the collagen content.

Wound strength was assessed by preparing rats substantially as described above, except that one group of rats (not irradiated) only received one injection of Halofuginone after wounding. The strength of wounds was measured as follows. First, a square of skin which was approximately 20 mm long and 16 mm wide, and which included the main part of the wound, was excised from sacrificed rats. Next, the skin was cut, perpendicular to the wound, to yield 7 strips of skin, each of which was 2 mm wide. The skin strips were secured between paper reinforcement frames and loaded on an Instron tensiometer for stretching at a constant rate of 25 mm/min. The bursting point was then recorded. Data are shown in FIG. 5 for non-irradiated animals which did not receive Halofuginone (column 1), non-irradiated animals which received one (column 2) or six (column 3) injections of Halofuginone, irradiated animals which did not receive Halofuginone (column 4) and irradiated animals which received six injections of Halofuginone (column 5).

Figure 5:
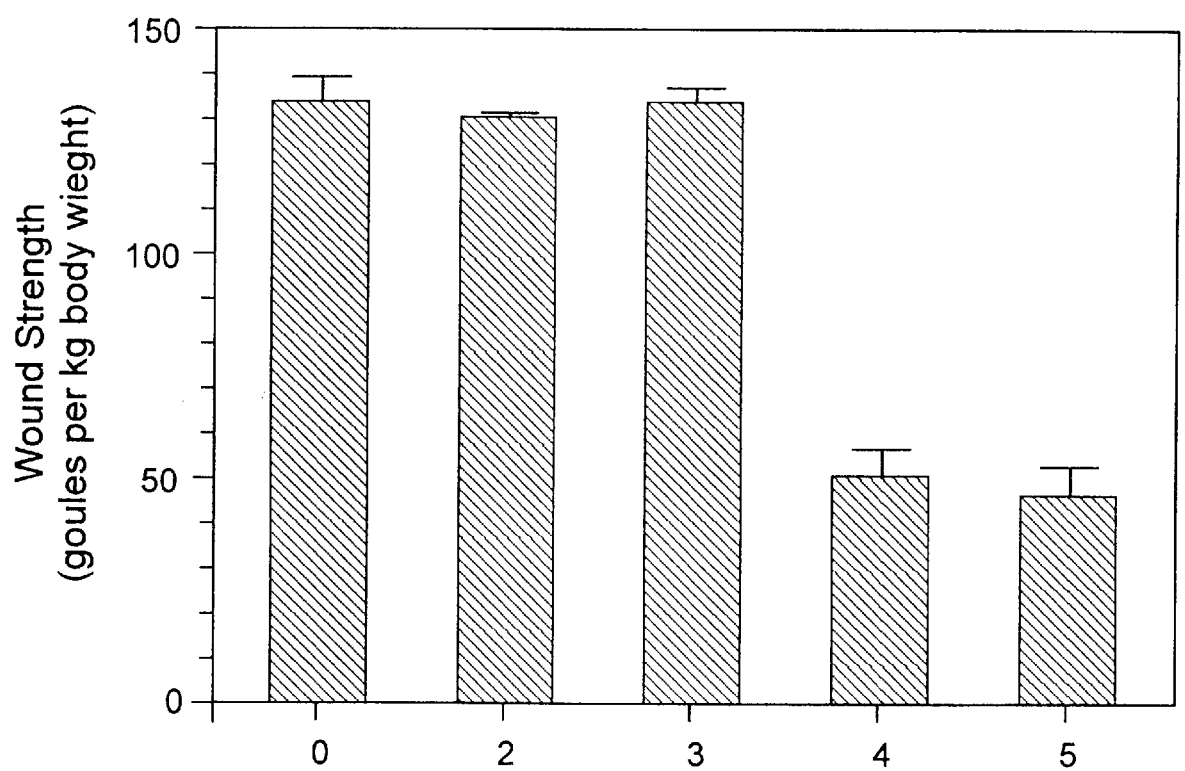
FIG. 5 illustrates the effect of Halofuginone on wound strength.

FIG. 5 clearly demonstrates that Halofuginone did not reduce wound strength, whether animals were irradiated or not. However, as noted above, the prior art teaches the importance of collagen for wound strength, so that Halofuginone would be expected to reduce such wound strength. Thus, the results obtained in FIGS. 4 and 5 are clearly novel and non-obvious, since Halofuginone does not reduce wound strength.

EXAMPLE 6

Suitable Formulations for Administration of Halofuginone

Halofuginone can be administered to a subject in a number of ways, which are well known in the art. Hereinafter, the term "subject" refers to the human or lower animal to whom Halofuginone was administered. For example, administration may be done topically (including ophtalmically, vaginally, rectally, intranasally), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the subject to Halofuginone. Persons of ordinary skill in the art can easily determine optimum dosages, dosing methodologies and repetition rates.

EXAMPLE 7

Methods of Treatment of Scars and Adhesions

As noted above, Halofuginone has been shown to be an effective inhibitor of scar and adhesion formation. The following examples are illustrations only of methods of treating scars and adhesions with Halofuginone, and are not intended to be limiting.

The method includes the step of administering Halofuginone, in a pharmaceutically acceptable carrier as described in Example 6 above, to a subject to be treated. Halofuginone is administered according to an effective dosing methodology, preferably until a predefined endpoint is reached, such as the absence of clinical symptoms in the subject. For example, if a subject already had an adhesion, the endpoint could be the reduction in size of the adhesion or its elimination.

Halofuginone can also be used as a pretreatment, administered to a subject before surgery to substantially prevent the formation of scars and adhesions. Of course, such a pretreatment would be most effective for scheduled surgery, as that would allow Halofuginone to be administered for a sufficient period of time before surgery to be most effective.

Another method of treatment would include the administration of Halofuginone, either alone or alternatively and preferably in combination with an antibiotic, for the treatment of inflammatory disease. Such a treatment would be particularly useful for the treatment of pelvic inflammatory disease, in which adhesion formation is induced by a bacterial infection in the reproductive organs of a woman.

Yet another method of treatment would include the administration of Halofuginone, in a pharmaceutically acceptable carrier, for the prevention of scar formation in the eyes, Scar formation in the eyes is particularly problematic because it can lead to an obstruction of vision from the affected eye. However, the most widely used inhibitor of scar formation, steroids, cannot be used in the presence of a viral optical infection, such as infection by the Herpes simplex virus. Steroids promote the proliferation of such viruses, rendering them dangerous to subjects undergoing eye surgery who have a viral optical infection. There is thus an unmet medical need for a compound which can inhibit scar formation in the eye, yet which does not promote viral proliferation. Halofuginone fills that need, since it has been demonstrated to inhibit scar formation, yet does not promote viral proliferation.

EXAMPLE 8

Method of Manufacture of a Medicament Containing Halofuginone

The following is an example of a method of manufacturing Halofuginone. First, Halofuginone is synthesized in accordance with good pharmaceutical manufacturing practice. Examples of methods of synthesizing Halofuginone, and related quinazolinone derivatives, are given in U.S. Pat. No. 3,338,909. Next, Halofuginone is placed in a suitable pharmaceutical carrier, as described in Example 6 above, again in accordance with good pharmaceutical manufacturing practice.

While the invention has been described with respect to a limited number of embodiments, it will be appreciated that many variations, modifications and other applications of the invention may be made.

What is claimed is:

1. A method for the treatment of an adhesion in a subject, the adhesion forming a fibrous bridge between normally separated tissues, with the proviso that the adhesion is not a fibrous peritendinous adhesion, the method comprising the step of administering to the subject a pharmaceutically effective amount of a compound having a formula:

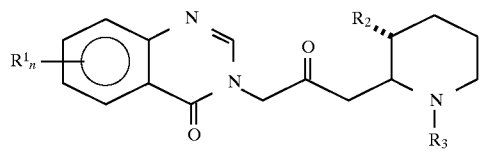

wherein:
$R_1$ is a member of the group consisting of hydrogen, halogen, nitro, benzo, lower alkyl, phenyl and lower alkoxy;
$R_2$ is a member of the group consisting of hydroxy, acetoxy and lower alkoxy, and
$R_3$ is a member of the group consisting of hydrogen and lower alkenoxy-carbonyl, such that the fibrous bridge is treated.

2. The method of claim 1, wherein the adhesion is within an abdominal cavity.

3. The method of claim 2, wherein the adhesion arises from a cause selected from the group consisting of surgical intervention in said abdominal cavity, presence of a foreign body in said abdominal cavity, inflammation of a tissue in said abdominal cavity, trauma to said abdominal cavity, irradiation of said abdominal cavity, presence of a tumor in said abdominal cavity and administration of a drug capable of inducing an adhesion in the subject.

4. The method of claim 3, wherein said inflammation of said tissue is caused by microbial infection of said tissue.

5. The method of claim 4, wherein said inflammation is of a reproductive organ of a female subject.

6. The method of claim 1, wherein said compound is Halofuginone.

7. A method for substantially preventing formation of an adhesion in a subject, the adhesion forming a fibrous bridge between normally separated tissues, with the proviso that the adhesion is not a fibrous peritendinous adhesion, the method comprising the step of administering to the subject a pharmaceutically effective amount of a compound having a formula:

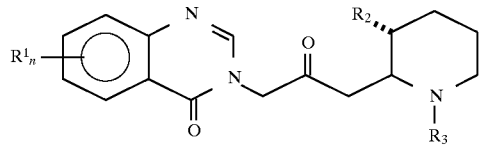

wherein:
$R_1$ is a member of the group consisting of hydrogen, halogen, nitro, benzo, lower alkyl, phenyl and lower alkoxy;
$R_2$ is a member of the group consisting of hydroxy, acetoxy and lower alkoxy, and
$R_3$ is a member of the group consisting of hydrogen and lower alkenoxy-carbonyl, such that the formation of the fibrous bridge is prevented.

8. The method of claim 7, wherein the adhesion is within an abdominal cavity.

9. The method of claim 8, wherein the cause of the adhesion arises is selected from the group consisting of surgical intervention in said abdominal cavity, presence of a foreign body in said abdominal cavity, inflammation of a tissue in said abdominal cavity, trauma to said abdominal cavity, irradiation of said abdominal cavity, presence of a tumor in said abdominal cavity and administration of a drug capable of inducing an adhesion in the subject.

10. The method of claim 9, wherein said inflammation of said tissue is caused by microbial infection of said tissue.

11. The method of claim 10, wherein said inflammation is of a reproductive organ of a female subject.

12. The method of claim 7, wherein said compound is Halofuginone.

13. A method for inhibition of formation of an adhesion in a subject for treatment substantially before performance of a surgical procedure, the adhesion forming a fibrous bridge between normally separated tissues, with the proviso that the adhesion is not a fibrous peritendinous adhesion, the method comprising the step of administering to the subject a pharmaceutically effective amount of a compound having a formula:

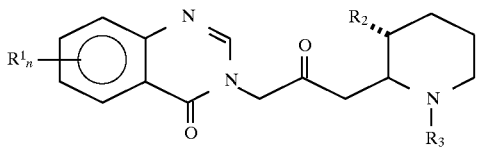

wherein:
$R_1$ is a member of the group consisting of hydrogen, halogen, nitro, benzo, lower alkyl, phenyl and lower alkoxy;
$R_2$ is a member of the group consisting of hydroxy, acetoxy and lower alkoxy, and
$R_3$ is a member of the group consisting of hydrogen and lower alkenoxy-carbonyl, such that the formation of the fibrous bridge is prevented.

14. The method of claim 13, wherein said compound is Halofuginone.

15. The method of claim 14, wherein the surgical procedure is performed in an abdominal cavity.

16. The method of claim 15, wherein the adhesion causes intestinal obstruction in the subject.

17. The method of claim 15, wherein the adhesion causes infertility in the subject.

18. A method for treatment of an inflammatory disease characterized by formation of an adhesion, the adhesion forming a fibrous bridge between normally separated tissues, with the proviso that the adhesion is not a fibrous peritendinous adhesion, the method comprising the step of administering to the subject a pharmaceutically effective amount of an antibiotic with a pharmaceutically effective amount of a compound having a formula:

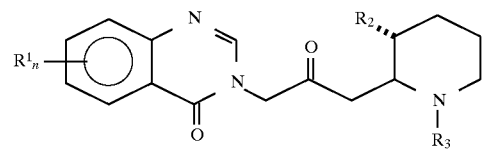

wherein:
$R_1$ is a member of the group consisting of hydrogen, halogen, nitro, benzo, lower alkyl, phenyl and lower alkoxy;
$R_2$ is a member of the group consisting of hydroxy, acetoxy and lower alkoxy, and
$R_3$ is a member of the group consisting of hydrogen and lower alkenoxy-carbonyl, such that the fibrous bridge is treated.

19. The method of claim 18, wherein the inflammatory disease is pelvic inflammatory disease.

20. The method of claim 18, wherein said compound is Halofuginone.

* * * * *